(12) United States Patent
Patterson et al.

(10) Patent No.: US 7,875,059 B2
(45) Date of Patent: Jan. 25, 2011

(54) VARIABLE STIFFNESS SUPPORT MEMBERS

(75) Inventors: Christopher M. Patterson, Olive Branch, MS (US); Michael S. Veldman, Memphis, TN (US); Randall Allard, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 760 days.

(21) Appl. No.: 11/624,401

(22) Filed: Jan. 18, 2007

(65) Prior Publication Data

US 2008/0177388 A1 Jul. 24, 2008

(51) Int. Cl.
*A61B 17/70* (2006.01)
(52) U.S. Cl. .................. 606/261; 606/254; 606/259
(58) Field of Classification Search ......... 606/246–279, 606/300–321, 63; 623/17.11–17.16, 23.32, 623/23.44–23.47
See application file for complete search history.

(56) References Cited

U.S. PATENT DOCUMENTS

| | | | |
|---|---|---|---|
| 5,217,461 A | 6/1993 | Asher et al. | |
| 5,415,661 A | 5/1995 | Holmes | |
| 5,486,174 A | 1/1996 | Fournet-Fayard et al. | |
| 5,591,164 A | 1/1997 | Nazre et al. | |
| 5,593,408 A | 1/1997 | Gayet et al. | |
| 5,997,542 A | 12/1999 | Burke | |
| 6,093,188 A | 7/2000 | Murray | |
| 6,099,528 A | 8/2000 | Saurat | |
| 6,102,912 A | 8/2000 | Cazin et al. | |
| 6,206,882 B1 | 3/2001 | Cohen | |
| 6,267,764 B1 | 7/2001 | Elberg et al. | |
| 6,296,644 B1 * | 10/2001 | Saurat et al. | 606/256 |
| 6,652,530 B2 | 11/2003 | Ip et al. | |
| 6,733,531 B1 | 5/2004 | Trieu | |

(Continued)

FOREIGN PATENT DOCUMENTS

FR 2799949 A1 4/2001

(Continued)

OTHER PUBLICATIONS

European Patent Office, International Searching Authority,Notification of Transmittal of the International Search Report and the Written Opinion of the International Searching Authority or the Declaration, International Application No. PCT/US2005/001067, May 17, 2005, 10 pages.

(Continued)

*Primary Examiner*—Eduardo C Robert
*Assistant Examiner*—Christina Negrelli

(57) ABSTRACT

Spinal support members having varying stiffnesses are disclosed. In one embodiment, an elongated spinal prosthetic includes a pair of curved elongated portions. The portions are formed of materials having different stiffness characteristics such that the stiffness of the prosthetic varies along its length. In another embodiment, an elongated spinal implant includes a pair of threadedly engaged elongated sections. The first section is formed of a first material having a first rigidity. The second section has an inner portion formed of the first material and an outer portion formed of a second material. The second material is less rigid than the first material. In another embodiment, a modular spinal rod is provided. The modular spinal rod includes a pair of connectable rod portions with different stiffness characteristics. In yet another embodiment, a kit for a modular spinal rod includes a plurality of connectable modular rod portions having different stiffness characteristics.

21 Claims, 7 Drawing Sheets

U.S. PATENT DOCUMENTS

| | | | |
|---|---|---|---|
| 6,966,910 | B2 | 11/2005 | Ritland |
| 6,986,771 | B2 | 1/2006 | Paul et al. |
| 6,989,011 | B2 * | 1/2006 | Paul et al. .............. 606/250 |
| 2003/0032958 | A1 * | 2/2003 | Soubeiran ............... 606/61 |
| 2003/0171749 | A1 | 9/2003 | Le Couedic et al. |
| 2004/0002708 | A1 | 1/2004 | Ritland |
| 2004/0049189 | A1 | 3/2004 | Le Couedic et al. |
| 2004/0102777 | A1 | 5/2004 | Huebner |
| 2004/0147928 | A1 | 7/2004 | Landry et al. |
| 2004/0215191 | A1 | 10/2004 | Kitchen |
| 2004/0267260 | A1 | 12/2004 | Mack et al. |
| 2005/0065515 | A1 | 3/2005 | Jahng |
| 2005/0065516 | A1 | 3/2005 | Jahng |
| 2005/0085815 | A1 | 4/2005 | Harms et al. |
| 2005/0124991 | A1 | 6/2005 | Jahng |
| 2005/0143823 | A1 | 6/2005 | Boyd et al. |
| 2005/0149020 | A1 | 7/2005 | Jahng |
| 2005/0154390 | A1 | 7/2005 | Biedermann et al. |
| 2005/0171539 | A1 | 8/2005 | Braun et al. |
| 2005/0177157 | A1 | 8/2005 | Jahng |
| 2005/0203511 | A1 | 9/2005 | Wilson-MacDonald et al. |
| 2005/0203513 | A1 | 9/2005 | Jahng et al. |
| 2005/0203514 | A1 | 9/2005 | Jahng et al. |
| 2005/0203517 | A1 | 9/2005 | Jahng |
| 2005/0203518 | A1 | 9/2005 | Biedermann et al. |
| 2005/0203519 | A1 | 9/2005 | Harms et al. |
| 2005/0209593 | A1 | 9/2005 | Kolb |
| 2005/0209694 | A1 | 9/2005 | Loeb |
| 2005/0261686 | A1 | 11/2005 | Paul |
| 2005/0267471 | A1 | 12/2005 | Biedermann et al. |
| 2005/0277922 | A1 | 12/2005 | Trieu et al. |
| 2005/0277926 | A1 | 12/2005 | Farris |
| 2005/0277932 | A1 | 12/2005 | Farris |
| 2006/0009768 | A1 | 1/2006 | Ritland |
| 2006/0041259 | A1 | 2/2006 | Paul et al. |
| 2006/0064090 | A1 | 3/2006 | Park |
| 2006/0079953 | A1 | 4/2006 | Gregorich et al. |
| 2006/0084982 | A1 | 4/2006 | Kim |
| 2006/0084984 | A1 | 4/2006 | Kim |
| 2006/0084987 | A1 | 4/2006 | Kim |
| 2006/0095134 | A1 | 5/2006 | Trieu |
| 2006/0129147 | A1 | 6/2006 | Biedermann et al. |
| 2006/0142758 | A1 | 6/2006 | Petit |
| 2006/0142760 | A1 | 6/2006 | McDonnell |
| 2006/0155279 | A1 | 7/2006 | Ogilvie |
| 2006/0184171 | A1 | 8/2006 | Biedermann et al. |
| 2006/0241769 | A1 * | 10/2006 | Gordon et al. ........... 623/17.13 |

FOREIGN PATENT DOCUMENTS

| | | | |
|---|---|---|---|
| GB | 238304 | A | 5/2003 |
| WO | WO0145576 | A1 | 6/2001 |

OTHER PUBLICATIONS

Sherman et al, Vertebral Stabilizer, U.S. Appl. No. 11/413,448, filed Apr. 28, 2006.

* cited by examiner

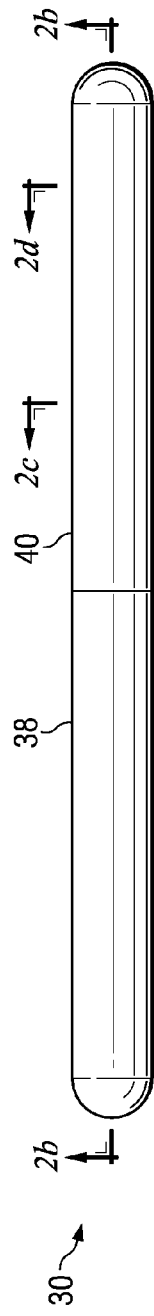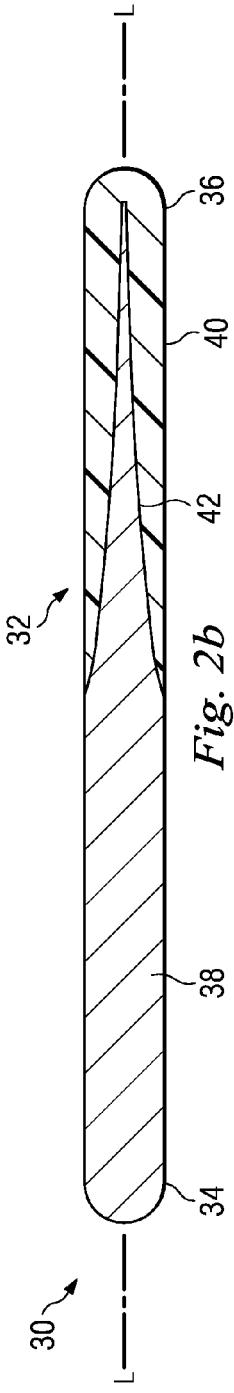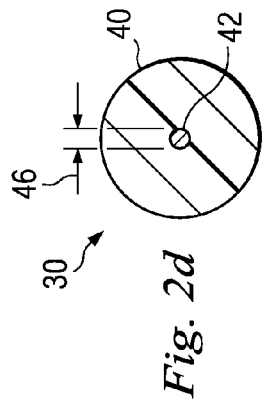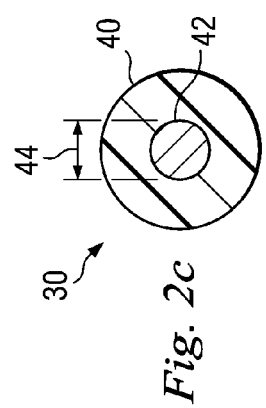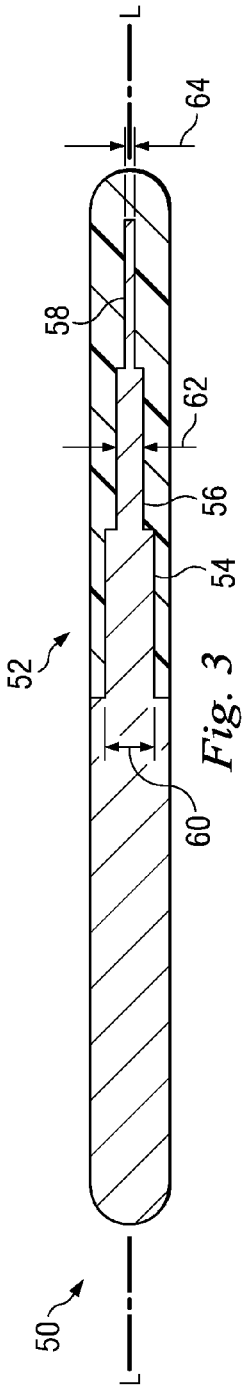

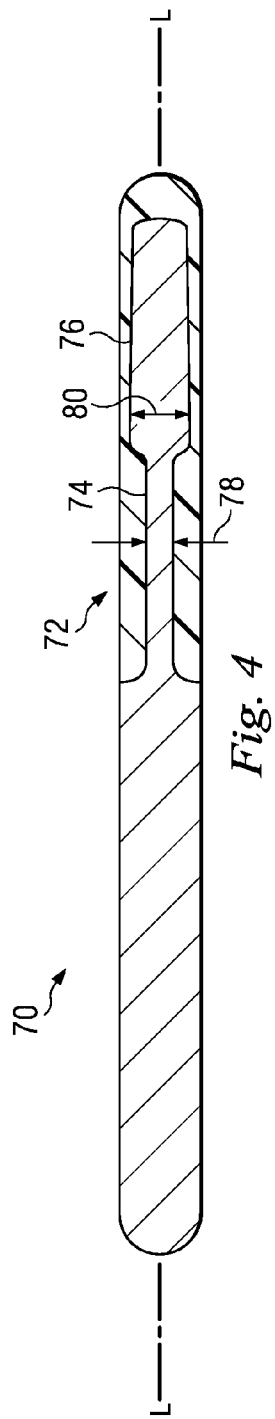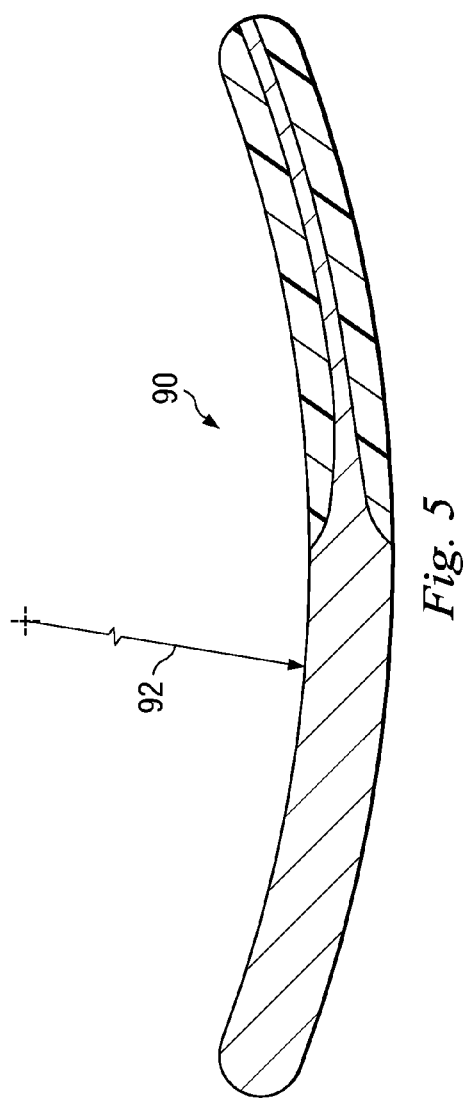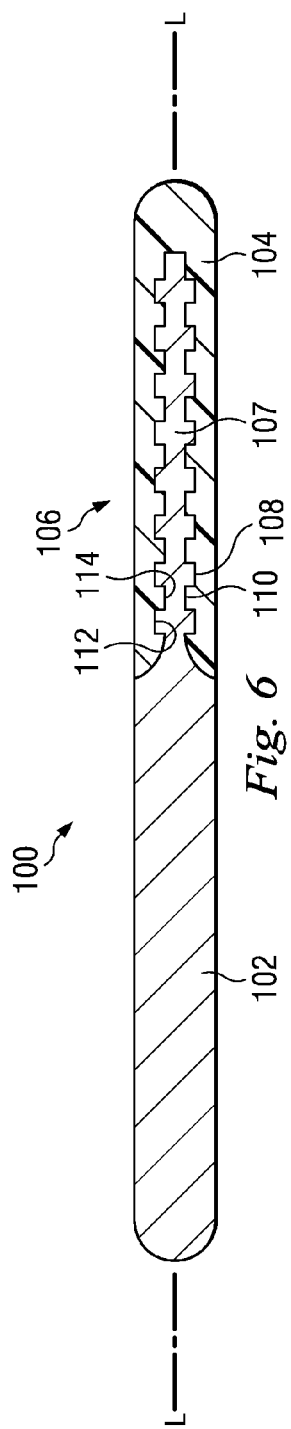

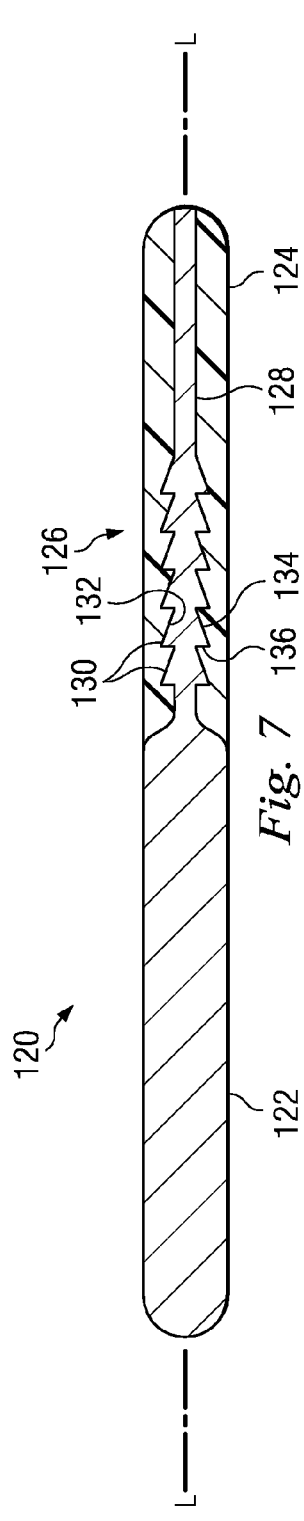
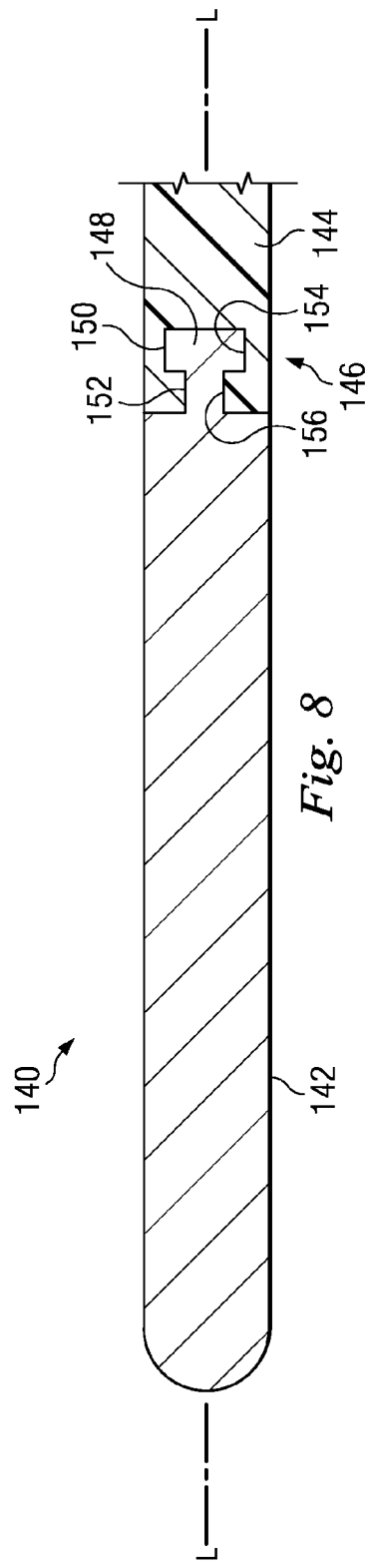
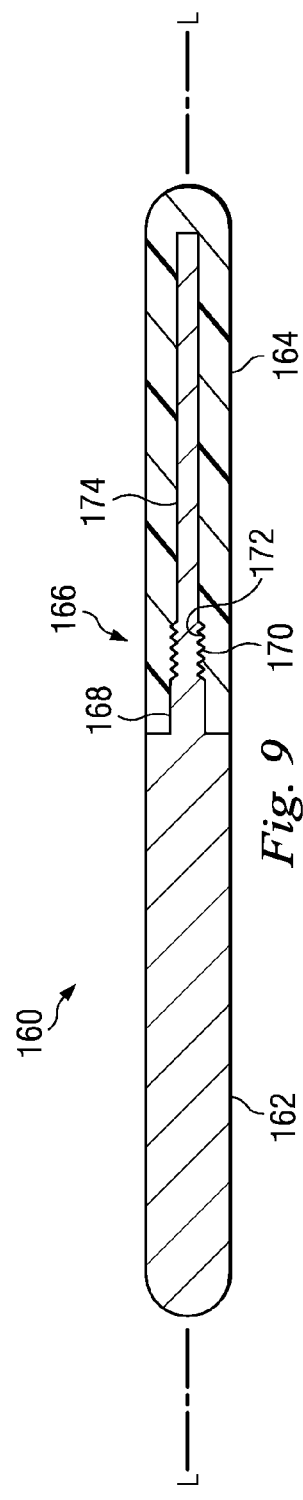

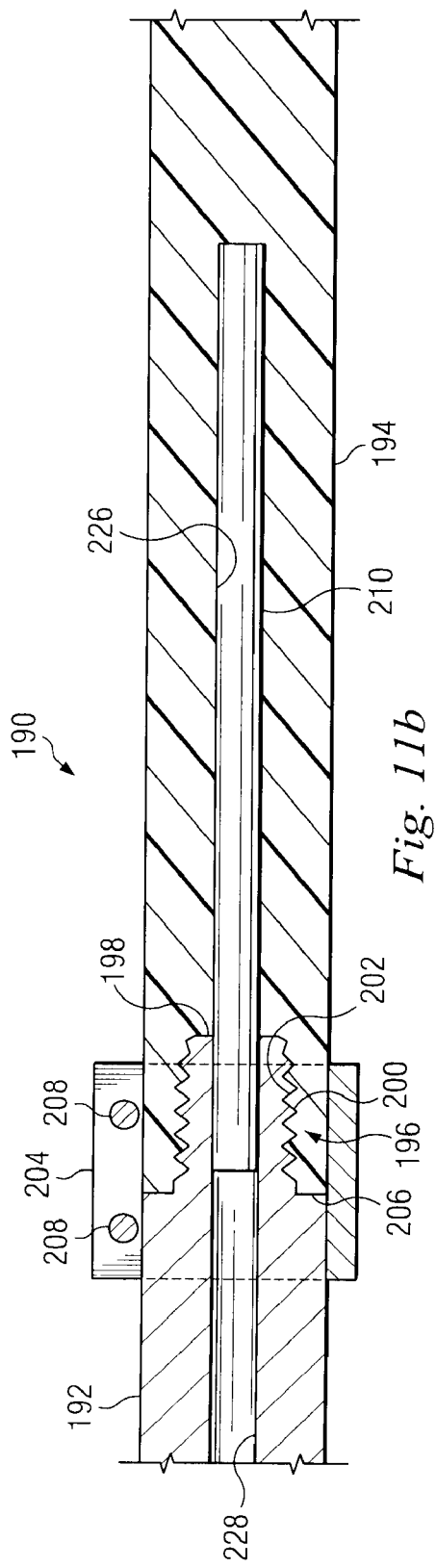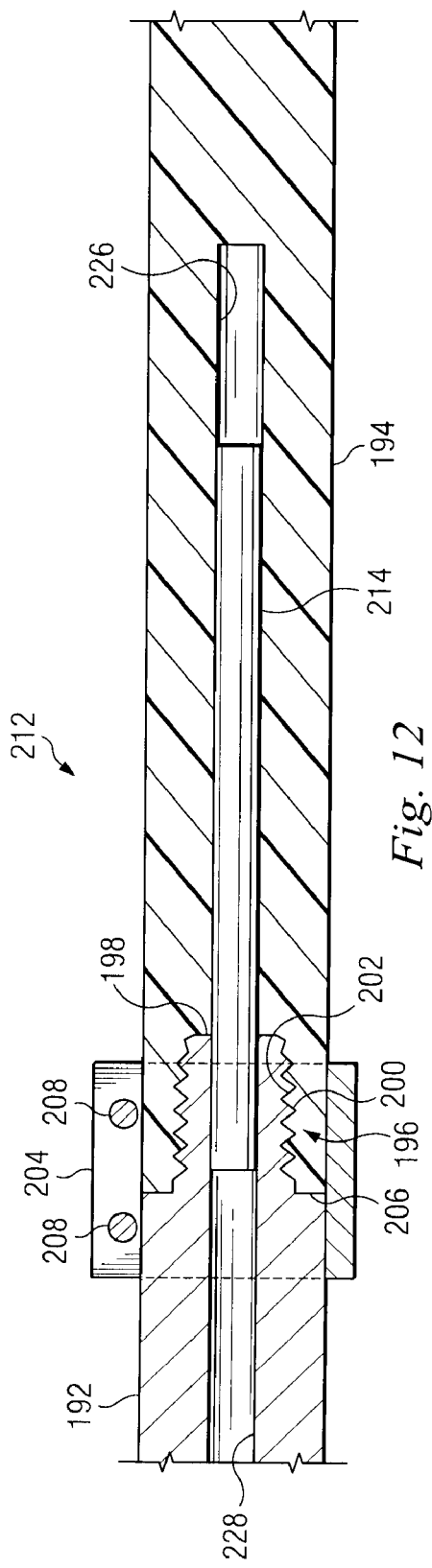

_US 7,875,059 B2_

VARIABLE STIFFNESS SUPPORT MEMBERS

TECHNICAL FIELD

Embodiments of the present disclosure relate generally to spinal support members and spinal stabilization systems. In some embodiments, the present disclosure relates to spinal rods having variable stiffness.

BACKGROUND

Although existing devices and methods have been generally adequate for their intended purposes, they have not been entirely satisfactory in all respects.

SUMMARY

In one embodiment, a support member having a varying stiffness along its length is disclosed.

In a second embodiment, an elongated spinal prosthetic is disclosed. The spinal prosthetic includes a pair of elongated portions. The first elongated portion has a male connection mechanism extending from one end. The first elongated portion is formed of a first material having a first rigidity. The second elongated portion has a female connection mechanism. The female connection mechanism is for receiving the male connection mechanism of the first elongated portion to connect the first and second elongated portions. The second elongated portion is formed of a second material different from the first material. In at least one embodiment, the second material has a second rigidity less than the first rigidity of the first material. In one embodiment, at least one of the first and second elongated portions is curved. In a further embodiment, the first elongate portion is threadedly engaged with the second elongated portion.

In another embodiment, a modular spinal rod is provided. The spinal rod includes a pair of rod portions. The first rod portion has a first connection mechanism extending from one end. The first rod portion is formed of a first material having a first rigidity. The second rod portion has a second connection mechanism for selective engagement with the first connection mechanism of the first rod portion to securely engage the first and second rod portions. The second rod portion is formed of a second material different from the first material. The second material has a second rigidity less than the first rigidity of the first material. In some embodiments, the modular spinal rod includes a third rod portion. The third rod portion is adapted to selectively engage with the second rod portion. The third rod portion is formed of a third material. The third material has a third rigidity less than the second rigidity of the second material.

In another embodiment, a kit is provided. The kit for a modular spinal rod includes a plurality of modular rod portions. Each of the plurality of rod portions is connectable to at least one of the other rod portions to form a spinal rod. A majority of the plurality of rod portions each have different stiffness characteristics such that rod portions with different stiffness characteristics may be connected to form a spinal rod with varying degrees of stiffness along its length.

Additional and alternative features, uses, and embodiments are set forth in or will be apparent from the following description, drawings, and claims.

BRIEF DESCRIPTION OF THE DRAWINGS

FIG. 2a is a diagrammatic side view of a spinal support member according to one aspect of the present disclosure.

FIG. 2b is a cross-sectional view of the spinal support member of FIG. 2a taken along section line 2b-2b.

FIG. 2c is a cross-sectional view of the spinal support member of FIG. 2a taken along section line 2c-2c.

FIG. 2d is a cross-sectional view of the spinal support member of FIG. 2a taken along section line 2d-2d.

FIG. 3 is a diagrammatic, cross-sectional side view of a spinal support member similar to FIG. 2b, but showing an alternative embodiment of the present disclosure.

FIG. 4 is a diagrammatic, cross-sectional side view of a spinal support member similar to FIGS. 2b and 3, but showing an alternative embodiment of the present disclosure.

FIG. 5 is a diagrammatic, cross-sectional side view of a spinal support member similar to FIGS. 2b, 3, and 4, but showing an alternative embodiment of the present disclosure.

FIG. 6 is a diagrammatic, cross-sectional side view of a spinal support member similar to FIGS. 2b and 3-5, but showing an alternative embodiment of the present disclosure.

FIG. 7 is a diagrammatic, cross-sectional side view of a spinal support member similar to FIGS. 2b and 3-6, but showing an alternative embodiment of the present disclosure.

FIG. 8 is a diagrammatic, cross-sectional side view of a spinal support member similar to FIGS. 2b and 3-7, but showing an alternative embodiment of the present disclosure.

FIG. 9 is a diagrammatic, cross-sectional side view of a spinal support member similar to FIGS. 2b and 3-8, but showing an alternative embodiment of the present disclosure.

FIG. 11b is a diagrammatic, cross-sectional side view of a spinal support member similar to FIGS. 2b and 3-10, but showing an alternative embodiment of the present disclosure.

FIG. 12 is a diagrammatic, cross-sectional side view of a spinal support member similar to FIGS. 2b, 3-10, and 11b, but showing an alternative embodiment of the present disclosure.

DESCRIPTION

Figure 1A:
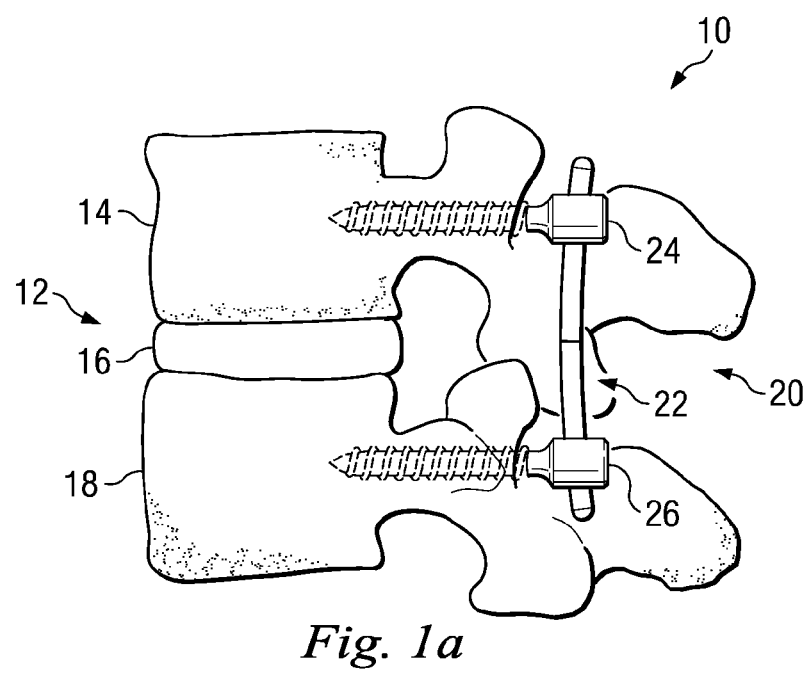
FIG. 1a is a diagrammatic side view of an arrangement that embodies aspects of the present disclosure.

For the purpose of promoting an understanding of the principles of the invention, reference will now be made to the embodiments, or examples, illustrated in the drawings and specific language will be used to describe the embodiments. It will nevertheless be understood that no limitation of the scope of the invention is intended. Any alterations and further modifications of the described embodiments, and any further applications of the principles of the invention as described herein are contemplated as would normally occur to one skilled in the art to which the invention relates.

FIG. 1a is a diagrammatic side view of an arrangement 10 that embodies aspects of the present invention. The arrangement 10 includes a motion segment 12. The motion segment 12 includes a superior vertebra 14, an intervertebral disc 16, and an inferior vertebra 18. As shown in FIG. 1, in one embodiment the motion segment 12 is a segment of the lumbar spine. More particularly, the superior vertebra 14 and inferior vertebra 18 represent vertebrae L4 and L5, respectively.

Figure 1B:
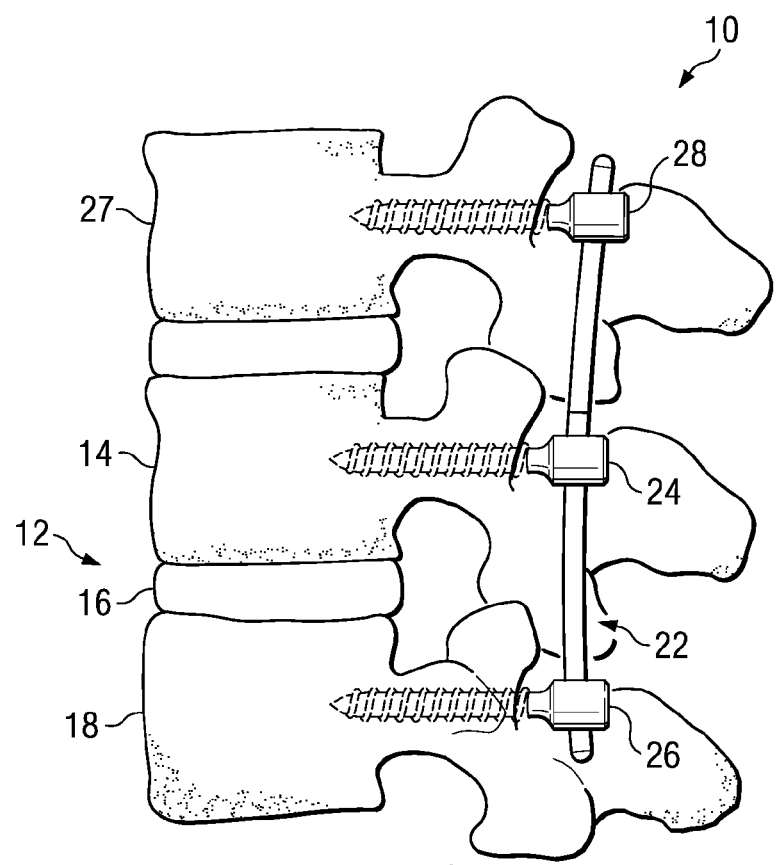
FIG. 1b is a diagrammatic side view of an arrangement similar to FIG. 1a, but showing an alternative embodiment of the present disclosure.

The arrangement 10 also includes a spinal implant 20. The spinal implant 20 includes an elongated spinal prosthetic or spinal support member 22 and fixation elements 24 and 26. As described in detail below, the stiffness of the spinal support member 22 varies along its length. In some embodiments, the variable stiffness of the spinal support member 22 is created by varying the material composition of the support member along its length. The fixation element 24 secures the spinal support member 22 to the superior vertebra 14 and the fixation element 26 secures the spinal support member to the inferior vertebra 18. As shown in FIG. 1b, in some embodiments the spinal support member 22 extends across multiple vertebral levels. In FIG. 1b, the support member 22 extends between vertebrae 14, 18, and 27. An additional fixation element 28 secures the support member to vertebra 27, as shown.

FIGS. 2a-14 and 16 illustrate various embodiments of the spinal support member 22 according to aspects of the present disclosure. FIGS. 2a-2d illustrate one embodiment of the present disclosure. FIG. 2a is a diagrammatic side view of a spinal support member 30 according to one embodiment of the present disclosure. FIG. 2b is a cross-sectional view of the spinal support member of FIG. 2a taken along section line 2b-2b. FIG. 2c is a cross-sectional view of the spinal support member of FIG. 2a taken along section line 2c-2c. FIG. 2d is a cross-sectional view of the spinal support member of FIG. 2a taken along section line 2d-2d.

The spinal support member 30 includes an elongated body portion 32 that extends substantially along its length between end portions 34 and 36. A longitudinal axis L extends substantially along the body portion 32 between the end portions 34 and 36. The end portions 34, 36 are adapted to mate with fixation elements to secure the support member 30 to the vertebrae. The fixation elements may be bone screws, staples, or any other suitable mechanism for securing the support member 30 to the vertebrae. In that regard, the end portions 34, 36 may include additional features that are not shown to facilitate use of the fixation elements.

In the current embodiment, the body portion 32 is comprised of two sections 38 and 40. As shown, section 38 includes a tapered region 42 that is substantially surrounded by section 40 and extends along a majority of the length of section 40. As shown in FIG. 2b, the tapered region 42 tapers at a substantially constant rate along its length. FIG. 2c shows a cross-sectional view of the support member 30 at a point where the diameter of the tapered region 42 has a width 44. FIG. 2d shows a cross-sectional view of the support member 30 at a point along the taper where the diameter of the tapered region has a width 46 that is less than the width 44. Further, as shown in FIGS. 2c and 2d the tapered region 42 is located centrally within section 40. However, in other embodiments the tapered region 42 is positioned off-center and/or tapers at a variable rate along its length. Further, the amount or degree of taper (or lack thereof) can be chosen to achieve the desired flexibility characteristics for the support member 30.

In the current embodiment, the two sections 38 and 40 are formed of materials having different stiffnesses. In particular, section 38 is formed of a material having a greater stiffness than the material of section 40. That is, the material of section 40 is more flexible than the material of section 38. In the current embodiment, section 34 is made substantially of titanium and section 40 is made of a polymer, such as polyetheretherketone ("PEEK"). Therefore, as the taper 42 of section 38 narrows within section 40 the support member 30 takes on more of the material properties of section 40. Thus, in the current embodiment the stiffness of the support member 30 decreases as it extends along its length from end portion 34 to end portion 36. In particular, the stiffness of the support member 30 decreases along section 40 as the taper 42 narrows. Though in the current embodiment section 38 is described as being stiffer than section 40, in other embodiments section 38 is more flexible than section 40.

As described below with respect to some exemplary embodiments, the flexibility/stiffness characteristics of the support member 30 may be varied in numerous ways. For example, the particular combination of materials of the sections 38, 40 may be chosen to define flexibility/stiffness characteristics along the length of the support member 30. For example, the sections 38, 40 may be formed from various combinations of other suitable biocompatible materials including metals, ceramics, polymers, and combinations thereof. For example, in some embodiments metals such as cobalt-chromium alloys, titanium alloys, nickel titanium alloys, and stainless steel alloys are suitable for at least one of the sections 38, 40. In other embodiments, ceramic materials such as aluminum oxide or alumina, zirconium oxide or zirconia, compact of particulate diamond, or pyrolytic carbon are suitable for at least one of the sections 38, 40. In yet other embodiments polymer materials are used, including members of the polyaryletherketone (PAEK) family such as polyetheretherketone (PEEK), carbon-reinforced PEEK, other modified PEEK materials, or polyetherketoneketone (PEKK); polysulfone; polyetherimide; polyimide; ultra-high molecular weight polyethylene (UHMWPE); cross-linked UHMWPE; silicon, polycarbonate urethanes, and nano-material treated polymers.

Also, the structure or geometries of the sections 38, 40 can be varied to achieve different flexibility characteristics. Several such exemplary embodiments are described below with respect to FIGS. 2-14 and 16. In general, the relative sizes of the sections 38, 40 to one another can be varied to modify the flexibility of the support member 30. For example, section 38 may form a majority of the support member 30 compared to section 40, or vice-versa. Further, the diameter of section 38 may be larger than the diameter of section 40 to further increase the stiffness of section 38 compared to section 40. Further, the transition or overlap of the sections (e.g. taper 42 surrounded by section 40) can be varied to modify the flexibility of the support member 30. For example, the taper 42 may taper more quickly or more gradually. Further, the taper 42 may extend a shorter or longer distance. On the other hand, the taper 42 may be replaced by an alternative structure.

For example, FIG. 3 shows an exemplary embodiment of a spinal support member 50 having an alternative structure 52 being used in place of taper 42. In particular, the structure 52 is comprised of a series stepped portions 54, 56, and 58 having decreasing diameters 60, 62, and 64, respectively. In the current embodiment, the diameter 60 of portion 54 is larger than diameter 62 of portion 56, which is larger than diameter 64 of portion 58. However, in other embodiments, the portions 54, 56, 58 do not have sequentially decreasing diameters 60, 62, 64. For example, in some embodiments, the diameter 64 is greater than diameter 62. The chosen diameters of each portion may be tailored for the desired characteristics of the support member. Further, the structure 52 may include more or less stepped portions. As another example, FIG. 4 shows another exemplary embodiment of a spinal support member 70 having an alternative structure 72 being used in place of taper 42 and structure 52. In particular, the structure 72 is comprised of a two portions 74 and 76. Portion 74 has a diameter 78 that is less than a diameter 80 of portion 76. As appreciated by one skilled in the art, numerous other transitions may be utilized to define the flexibility of the support member 30.

Further, the structure or geometry of the support member 30 as a whole can be varied to achieve different flexibility characteristics along the length of the support member. Referring to FIG. 2, the support member 30 is substantially cylindrical along its length and may be considered a rod. That is, the support member 30 has a substantially circular cross-section that is substantially constant along its length. However, in other embodiments the support member 30 has various other cross-sections including polygonal, geometrical, and irregular shapes. Further, the cross-section of the support member 30 may be varied along its length to further the flexibility characteristics of the support member. In one exemplary embodiment, the section 38 has a cross-section that is different from the cross-section of section 40. Further, in another embodiment the body portion 32 has an oval cross-section and the end portions 34, 36 have substantially circular cross-sections. In some embodiments, the cross-section of the spinal support member is such that the support member can be considered a plate. In other embodiments, the spinal support member is a plate-rod combination.

The cross-sections of the body portion 32 and sections 38, 40 are varied in some embodiments to obtain desired physical properties, such as the appropriate stiffness/flexibility and support strength. The cross-section is tailored for the particular use of the spinal support member in some embodiments. For example, in one embodiment the cross-section is configured to match the desired flexibility and support for the region of the spine where the spinal support member is to be implanted. For example, the superior portion (e.g., section 40) of a spinal support member configured to extend between multiple vertebrae has a first cross-sectional area and the inferior portion (e.g., section 38) has a second cross-sectional area, with the second cross-sectional area being greater than the first. Such a support member is useful in treating scoliosis or in dynamic stabilization of the spine. In other embodiments, the support member 30 has cross-sectional areas with various combinations of larger, smaller, and different shaped cross-sections.

Referring to FIG. 2, the spinal support member 30 is illustrated as being substantially straight along its length. However, in other embodiments the spinal support member 30 is curved along its length. The curvature of the support member 30 can affect the flexibility characteristics of the support member. Thus, in some embodiments the support member 30 is curved along its length to define the stiffness of the support member along its length. Referring to FIG. 5, shown therein is a spinal support member 90 that is curved along its length according to an alternative embodiment of the present disclosure. In the illustrated embodiment, the spinal support member has a the radius of curvature 92. The radius of curvature 92 is substantially uniform along the length of spinal support member 90. In some embodiments, the radius of curvature 92 is between 50 mm and 200 mm. In other embodiments, the radius of curvature 92 is larger than 200 mm and, where the support member 30 is substantially straight approaches infinity. In yet other embodiments, the spinal support member has multiple radii of curvature along its length or a radius of curvature that changes along its length. Further, in some embodiments the spinal support member curves in multiple directions. For example, the support member may have multiple curves along its length to accommodate the transition between lumbar and thoracic curvatures, and between thoracic and cervical curvatures.

The curvature of the spinal support member can be tailored to define the flexibility characteristics for the support member based on the intended use of the support member. In that regard, the spinal support member may be used in the cervical, thoracic, and lumbar regions of the spine and, in some embodiments, the spinal support member may extend across multiple regions of the spine. For example, the shape and the radius of curvature is adjusted to match the lordosis or kyphosis for the region of the spine where the spinal support member is to be implanted. Further, the shape and the radius of curvature is adjusted to match the required support for the region of the spine where the spinal support member is to be implanted. Support members utilized to treat scoliosis may include curves extending in the anterior-posterior plane as well as in the medial-lateral plane. In a further embodiment, the elongated fixation member includes a support member portion and a plate portion joined to the support member portion. This may find particularly useful application in joining the spine to a portion of the head. In still a further embodiment, the elongated fixation member is a curved plate having one or more holes extending therethrough adapted to receive bone engagement fasteners.

Further, as illustrated and described above, the spinal support member 30 is substantially symmetrical such that it may be used on both the left and right sides of the spine. In other embodiments, however, the spinal support member is designed for placement specifically on either the left or right side of the spine. The spinal support member can be tailored for placement on a particular side by changing the general shape, the radius of curvature, the cross-section, or other appropriate features of the spinal support member. In this regard, the general shape, the radius of curvature, the cross-section, or other appropriate features of the support member may be chosen to define the desired flexibility characteristics of the support member based on the side of the spine it will be placed.

In some embodiments, the spinal support member 30 is manufactured such that the sections 38 and 40 are formed as an integral piece. For example, in some embodiments section 40 is molded over a preformed section 38. However, in other embodiments the spinal support member 30 is manufactured such that the sections 38 and 40 are separate pieces that are joined together to form the spinal support member. The sections 38 and 40 may be joined in numerous ways. For example, the sections 38 and 40 may be joined by mating structures of the sections, using adhesives, or otherwise connecting the sections. In this manner, sections may be combined to create a modular spinal support member with a varying stiffness. The sections of the modular spinal support member may be chosen to achieve a desired flexibility characteristic of the support member in that section and to define the overall flexibility of the support member. In some embodiments, all or a portion of the support member is molded as described in U.S. patent application Ser. No. 11/469,354, entitled "Polymer Support members for Spinal Applications," filed Aug. 31, 2006, herein incorporated by reference in its entirety.

In that regard, in some embodiments a kit is provided having a plurality of spinal support member sections with varying flexibility characteristics that may be selectively joined together to form a spinal support member having varying degrees of stiffness along its length. Each of the spinal support member sections is configured to define a particular flexibility. Further, the kit may include multiple support member sections with substantially identical flexibility characteristics where similar stiffnesses may be desired at multiple locations along the support member.

FIGS. 6-9 show various exemplary embodiments of spinal support members according to aspects of the present invention and, in particular, show alternative ways of connecting two sections of a spinal support member. These embodiments are by no means an exhaustive representation of all of the ways of connecting two sections, but rather are included only as examples. Numerous other ways of connecting two sections of a spinal support member, structural and otherwise, would be apparent to one skilled in the art.

Referring to FIG. 6, shown therein is a spinal support member 100 according to an alternative embodiment of the present disclosure. The spinal support member 100 includes two sections 102 and 104. The two sections 102, 104 are connected to one another via a convoluted engagement structure 106. The convoluted engagement structure 106 includes a plurality of engaged projections and recesses, as shown. In particular, section 102 includes an elongated portion 107 having a series of alternating projections 108 and recesses 110. The projections 108 and recesses 110 of section 102 are adapted to mate with a corresponding series of alternating recesses 112 and projections 114 of section 104, as shown. Together the projections 108 and recesses 110 of section 102 and the recesses 112 and projections 114 of section 104 form the convoluted engagement structure 106. In the current embodiment, the projections extend substantially transverse to the longitudinal axis L of the support member 100. In other embodiments, the projections extend at an oblique angle relative to the longitudinal axis L. Further, in the current embodiment the surfaces of the projections and recesses are substantially planar. However, in other embodiments, the some or all of the surfaces of the projections and recesses may have curved or arcuate surfaces.

Referring to FIG. 7, shown therein is a spinal support member 120 according to an alternative embodiment of the present disclosure. The spinal support member 120 includes two sections 122 and 124. The two sections 122, 124 are connected to one another via an engagement structure 126. The engagement structure 126 includes a plurality of engaged projections and recesses, as shown. In particular, section 122 includes an elongated portion 128 having a series of angled projections 130 extending therefrom. The projections 130 of section 122 are adapted to mate with a corresponding series of recesses 132 of section 124, as shown. Together the projections 130 and of section 122 and the recesses 132 of section 124 form the engagement structure 106. In that regard, the projections 130 are angled such that facilitate one-way insertion of the elongated portion 128 within section 124. That is, the projections 130 are shaped to permit insertion of the elongated portion 128, but prevent the elongated portion from being retracted once the projections have engaged with the recesses 132 of section 124. In that regard, the projections 130 include a leading surface 134 that extends at an oblique angle from the longitudinal axis L of the support member 120. The projections 130 also include a trailing surface 136 extending between the elongated portion 128 to the leading surface 134 substantially perpendicular to the longitudinal axis L of the support member 120.

Referring to FIG. 8, shown therein is a spinal support member 140 according to an alternative embodiment of the present disclosure. The spinal support member 140 includes two sections 142 and 144. The two sections 142, 144 are connected to one another via an engagement structure 146. The engagement structure 146 includes a pair of engaged projections and recesses, as shown. In particular, section 142 includes an extension 148 having a broadened end portion 150. The broadened end portion 150 defines a recessed portion 152. The broadened end portion 150 engages with a recess 154 of section 144 defined by a projection 156, as shown. Further, the projection 156 engages the recessed portion 152 of extension 148 of section 142. Together the engagement of the projections 150, 156 with the recesses 152, 154 form the engagement structure 146. In one embodiment, the section 144 is over-molded onto the extension 148.

Referring to FIG. 9, shown therein is a spinal support member 160 according to an alternative embodiment of the present disclosure. The spinal support member 160 includes two sections 162 and 164. The two sections 162, 164 are connected to one another via a threaded engagement structure 166. In particular, section 162 includes an extension 168 having threads 170 extending therefrom. The threads 170 mate with the threaded recesses 172 of section 164. The extension 168 also includes an elongated member 174 extending within and along a majority of the length of section 164. In the current embodiment, the member 174 is an elongated support member formed of material having a greater stiffness than the material forming section 164. In some embodiments, the member 174 is formed of the same material as section 162. The member 174 is adapted to increase the stiffness of section 164.

In other embodiments, the member 174 is part of section 164 or piece separate from each of the sections 162, 164. In some embodiments, the member 174 is not inserted into section 164. In such embodiments, section 164 may have a hollow opening extending therethrough or may have an alternative member inserted. For example, in some embodiments the member is made of substantially the same material as section 164. In some embodiments, the member 174 is formed of a material having equal or more flexibility than the material of section 164. In some embodiments, the member 174 extends substantially along the length of section 164. In other embodiments, the member 174 extends along only a portion of the length of section 164.

Figure 10:
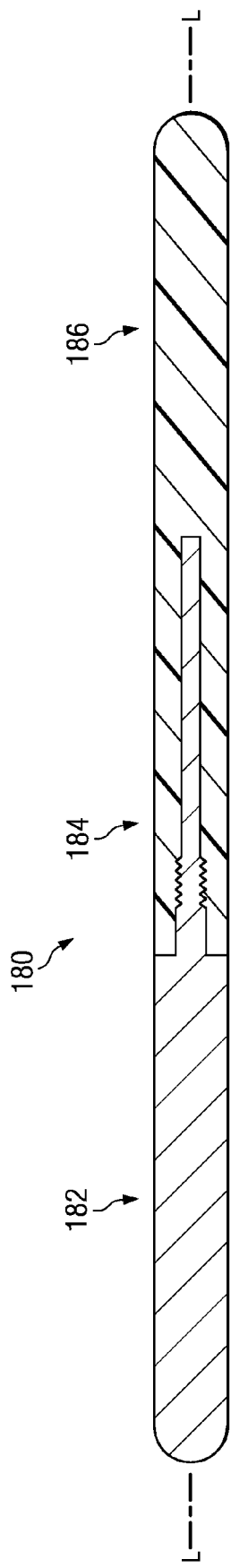
FIG. 10 is a diagrammatic, cross-sectional side view of a spinal support member similar to FIGS. 2b and 3-9, but showing an alternative embodiment of the present disclosure.

Referring now to FIG. 10, shown therein is a spinal support member 180 according to an alternative embodiment of the present disclosure. The spinal support member 180 includes three sections 182, 184, and 186. Sections 182 and 184 are substantially similar to sections 162 and 164 described above with respect to FIG. 9. Section 186 is comprised entirely of the material of section 164 and does not have a member 174 extending therein. Thus, the spinal support member 180 illustrates an embodiment having increasing degrees of flexibility along its length. That is, section 182 is formed entirely of a first material having a first stiffness; section 184 is formed partially of the first material of section 182 and partially of a second material having second stiffness that is less than the first material; and section 186 is formed entirely of the second material. In some embodiments, the spinal support member 180 is sized to extend between two vertebrae. In other embodiments, the spinal support member 180 is sized to extend between at least three vertebrae.

Figure 11A:
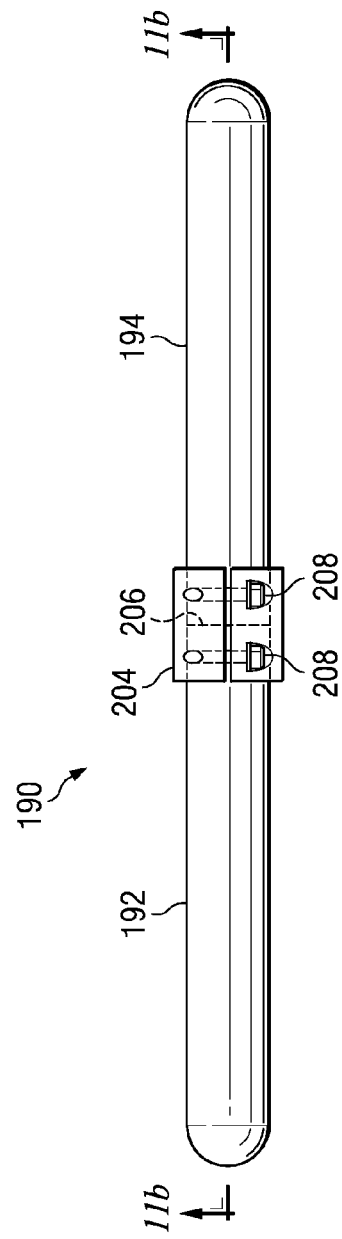
FIG. 11a is a diagrammatic side view of a spinal support member similar to FIG. 2a above, but showing an alternative embodiment of the present disclosure.

Referring now to FIGS. 11a and 11b, shown therein is a spinal support member 190 according to an alternative embodiment of the present disclosure. The spinal support member 190 includes two sections 192 and 194. The two sections 192, 194 are connected to one another via a threaded engagement structure 196. Similar to spinal support member 160 above, section 192 includes an extension 198 having threads 200 extending therefrom. The threads 200 mate with the threaded recesses 202 of section 194. As shown in FIG. 11b, the spinal support member 190 also includes a sleeve member 204. The sleeve member 204 is positioned adjacent the outer transition 206 between section 192 and section 194. The sleeve member 204 is adapted to protect the transition 206 from unwanted wear and/or damage due to stress on the transition of the support member 190.

In the current embodiment, the sleeve member 204 is substantially coaxial with the support member 190. The sleeve member 204 is a compression sleeve such that it clamps onto the support member 190 and is tightened by screws 208. In other embodiments, the sleeve member 204 is secured by a single screw 208. In yet other embodiments, the sleeve member 204 is secured to the support member 190 via an alternative mechanism. For example, in some embodiments the sleeve member 204 is positioned adjacent the transition 206 in a first state and then heated, melted, or otherwise treated such that it moves into a second state that secures the sleeve member 204 to the support member and protects the transition. In other embodiments, the sleeve member 204 has an inner diameter slightly larger than the support member 190 such that it can be press-fit over the support member into position adjacent the transition 206. In some embodiments the sleeve member 204 is adapted to connect the sections 192, 194 to each other in addition to protecting the transition 206. In such embodiments, the sections 192, 194 may include additional features and/or structure to facilitate engagement with the sleeve member 204. Further, in some embodiments, the sleeve member 204 may be part of a fixation element adapted to secure the support member 190 to a vertebra. For example, the sleeve member 204 could be part of a hook, an offset rod connector, or other fixation device.

Figure 13:
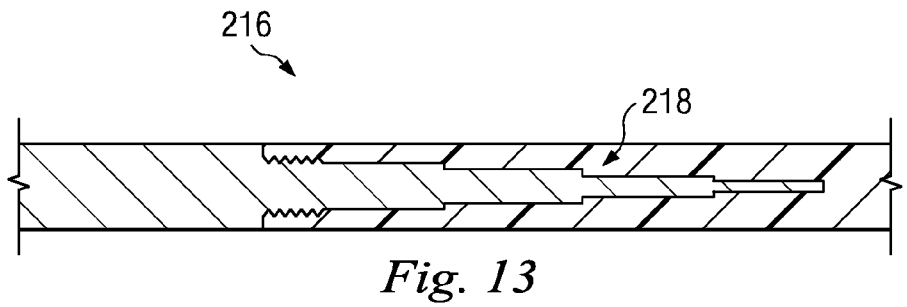
FIG. 13 is a diagrammatic, cross-sectional side view of a spinal support member similar to FIGS. 2b, 3-10, 11b, and 12, but showing an alternative embodiment of the present disclosure.
Figure 14:
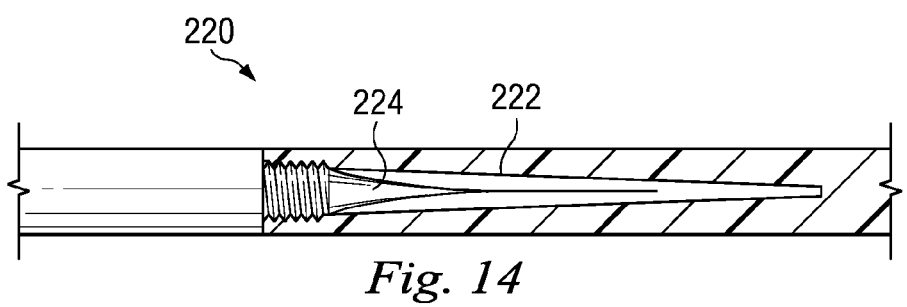
FIG. 14 is a diagrammatic, cross-sectional side view of a spinal support member similar to FIGS. 2b, 3-10, 11b, 12, and 13, but showing an alternative embodiment of the present disclosure.

Referring more specifically to FIG. 11b, the spinal support member 190 also includes a stiffening member 210 extending within and along a majority of the length of section 194. In the current embodiment, the member 210 is an elongated support member formed of material having a stiffness greater than the stiffness of the material forming section 194. In some embodiments, the member 210 is formed of the same material as section 192. The member 210 is adapted to increase the stiffness of section 194. In that regard, the characteristics of the member 210 may be chosen based on the desired stiffness characteristics of the support member 190 and, in particular, section 194. That is, such features as the material, length, and shape of the member 210 may be tailored to fit the desired flexibility of the support member 190. For example, FIG. 12 illustrates a spinal support member 212 having a stiffening member 214 similar to stiffening member 210, but having a shorter length. FIG. 13 illustrates a spinal support member 216 having a stepped stiffening member 218. FIG. 14 illustrates a spinal support member 220 having a tapered stiffening member 222. The stiffening member 222 is fluted. That is, the stiffening member 222 includes an groove or opening 224 extending at least partially along its length. Similar to the stiffening member 222 itself, the characteristics of the groove 224 can be chosen based on the desired flexibility characteristics of the stiffening member and, in turn, the spinal support member 220.

Referring again to FIG. 11b, in the current embodiment the stiffening member 210 is adapted to mate with an opening 226 of section 194. In that regard, section 192 includes an opening 228 extending along its length to allow the member 210 to pass therethrough into section 194. In some embodiments, the member 210 is sized to extend substantially across both opening 226 and opening 228. Further, in some embodiments the stiffening member 210 includes engagement features to secure it within the opening 226. For example, the stiffening member 210 may be threaded, include projections to engage recesses of the opening, be coated with an adhesive, be sized to be press-fit within the opening 226, or otherwise be adapted to securely mate with the opening 226. In some embodiments, the opening 226 is adapted to receive an end cap to secure the member 210 within the spinal support member 90. In some embodiments, the end cap is similar to the end caps described in U.S. patent application Ser. No. 11/469,354, entitled "Polymer Support members for Spinal Applications," filed Aug. 31, 2006, herein incorporated by reference in its entirety.

Figure 15:
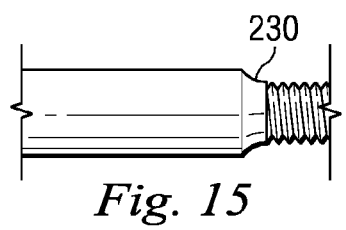
FIG. 15 is a diagrammatic side view of a connection member for use with the spinal support members of the present disclosure.

In addition to or in lieu of the sleeve member 204, the transition between sections 192 and 194 may be protected from stress and fatigue by the engagement structure 196. For example, as shown in FIG. 15 the extension 198 of section 192 may have a curved transition 230 extending to threads 200. In some embodiments, the curved transition 230 is more fatigue friendly than an abrupt or planar transition.

Figure 16:
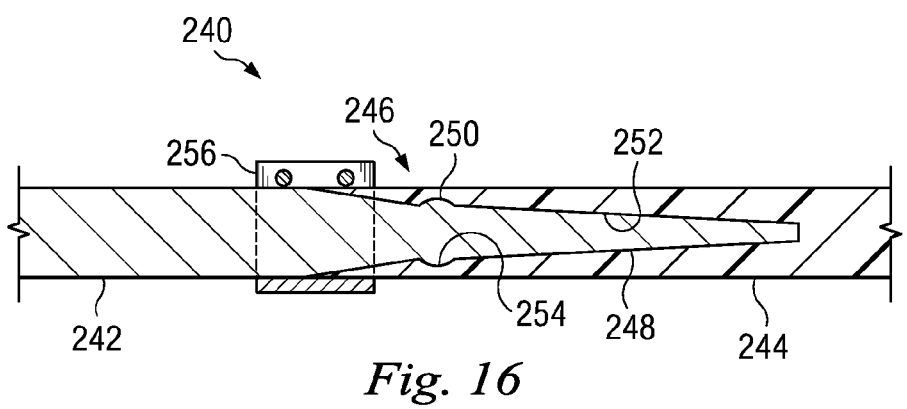
FIG. 16 is a diagrammatic, cross-sectional side view of a spinal support member similar to FIGS. 2b, 3-10, 11b, and 12-14, but showing an alternative embodiment of the present disclosure.

Referring to FIG. 16, shown therein is a spinal support member 240 according to an alternative embodiment of the present disclosure. The spinal support member 240 includes two sections 242 and 244. The two sections 242, 244 are connected to one another via an engagement structure 246. In the current embodiment, section 242 includes an elongated extension 248 having a protrusion 250 extending therefrom. The extension 248 is adapted to mate an elongated opening 252 of section 244. Further, the protrusion 250 is adapted to engage a recess 254 in the opening 252. In this manner section 242 and 244 can be snapped together to form spinal support member 240. By elongated the transition between the two sections 242 and 244 along the extension 248 and opening 252, the stress on the transition is transferred along the length of the transition reducing the chances of damage to the support member. The spinal support member 240 also includes a sleeve member 256, similar to sleeve 204 described above, to further protect the transition between the two sections 242, 244.

Further, the snap together feature of the present embodiment may be utilized to connect sections of a modular spinal support member. In that regard, a plurality of spinal support member sections having various material characteristics, such as varying stiffnesses, may be provided such that the surgeon can select the appropriate spinal support member sections to mate together to form a spinal support member having the desired material properties along its length through various sections. The spinal support member 190 also includes a sleeve member 204. The sleeve member 204 is positioned adjacent the outer transition 206 between section 192 and section 194. The sleeve member 204 is adapted to protect the transition 206 from unwanted wear and/or damage due to stress on the transition of the support member 190.

The spinal support members described above may also include visual guidance markers to assist the surgeon in properly orienting the spinal support members upon implantation. In one embodiment, the markers extend along each of the sides of the support member to provide the surgeon with an easily identifiable marking for orienting the spinal support member during implantation and fixation. In another embodiment, the markers comprise a radiopaque pin. The pin is positioned within the support member to provide visualization using fluoroscopy. A plurality of radiopaque pins are used in other embodiments. The pins may be placed anywhere along the length of the support member to assist in orienting the support member during implantation and fixation. The marker(s) can also be placed anywhere on the support member, including the front, back, top, bottom, and sides.

The spinal support members described above and the various portions and sections thereof, may be manufactured and/or joined together by machining, injection molding, overmolding, thermal staking, ultrasonic welding, and other suitable methods.

Other modifications of the present disclosure would be apparent to one skilled in the art. Accordingly, all such modifications and alternatives are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure. It is understood that all spatial references, such as "horizontal," "vertical," "top," "upper," "lower," "bottom," "left," and "right," are for illustrative purposes only and can be varied within the scope of the disclosure. In the claims, means-plus-function clauses are intended to cover the structures described herein as performing the recited function and not only structural equivalents, but also equivalent structures.

What is claimed is:

1. An elongated spinal prosthetic comprising:
    a first elongated portion having a male connection mechanism extending from one end, the first elongated portion having a first outer surface formed of a first material having a first rigidity, wherein the first outer surface has a first cylindrical profile along a majority of its length, the first cylindrical profile having a first diameter; and
    a second elongated portion having a female connection mechanism for receiving the male connection mechanism of the first elongated portion to fixedly connect the first and second elongated portions, the second elongated portion having a second outer surface formed of a second material different from the first material, the second material having a second rigidity less than the first rigidity of the first material,
    wherein the second outer surface has a second cylindrical profile along a majority of its length, the second cylindrical profile having a second diameter, the second diameter being substantially equal to the first diameter such that when the first and second elongated portions are connected via the male and female connection mechanisms the elongated spinal prosthetic has a substantially constant cylindrical profile along a majority of its length,
    wherein a majority of the first elongated portion is formed of the first material and wherein a majority of the second elongated portion is formed of the second material,
    wherein the first material is a metal and the second material is a polymer,
    wherein the first elongated portion is curved along its length,
    wherein a thickness of the male connection mechanism is varied along its length, and
    wherein the thickness of the male connection mechanism is tapered along its length.

2. The elongated spinal prosthetic of claim 1 wherein the first material is selected from the group of metals consisting of titanium alloys, cobalt-chromium alloys, nickel titanium alloys, and stainless steel alloys, and the second material is PEEK.

3. The elongated spinal prosthetic of claim 1 wherein the male connection mechanism extends within the second elongated portion along a majority of the length of the second elongated portion.

4. The elongated spinal prosthetic of claim 1 wherein the thickness of male connection mechanism decreases and increases along its length.

5. The elongated spinal prosthetic of claim 1 wherein the radii of curvature for the first and second elongated portions are substantially equal such that the elongated spinal prosthetic has a substantially continuous radius of curvature along its length.

6. The elongated spinal prosthetic of claim 1 further comprising a sleeve member positioned around the first and second elongated portions adjacent a junction between the first and second outer surfaces.

7. The elongated spinal prosthetic of claim 6 wherein the sleeve member comprises a clamp.

8. The elongated spinal prosthetic of claim 1 further comprising an end cap adapted to engage at least one end of at least one of the first and second elongated portions.

9. The elongated spinal prosthetic of claim 1 wherein the second elongated portion is molded over the first elongated portion.

10. The elongated spinal prosthetic of claim 1, wherein the radius of curvature for the first elongated portion is different from the radius of curvature for the second elongated portion such that the elongated spinal prosthetic has a varying radius of curvature along its length.

11. The elongated spinal prosthetic of claim 10 wherein the radius of curvature for the first elongated portion is curved in a direction substantially opposite the radius of curvature for the second elongated portion when the first and second portions are connected.

12. An elongated spinal prosthetic comprising:
    a first elongated portion having a male connection mechanism extending from one end, the first elongated portion having a first outer surface formed of a first material having a first rigidity, wherein the first outer surface has a first cylindrical profile along a majority of its length, the first cylindrical profile having a first diameter; and
    a second elongated portion having a female connection mechanism for receiving the male connection mechanism of the first elongated portion to fixedly connect the first and second elongated portions, the second elongated portion having a second outer surface formed of a second material different from the first material, the second material having a second rigidity less than the first rigidity of the first material,
    wherein the second outer surface has a second cylindrical profile along a majority of its length, the second cylindrical profile having a second diameter, the second diameter being substantially equal to the first diameter such that when the first and second elongated portions are connected via the male and female connection mechanisms the elongated spinal prosthetic has a substantially constant cylindrical profile along a majority of its length,
    wherein a majority of the first elongated portion is formed of the first material and wherein a majority of the second elongated portion is formed of the second material,
    wherein the first material is a metal and the second material is a polymer,
    wherein the first elongated portion is curved along its length,
    wherein the second elongated portion is curved along its length, and wherein the radius of curvature for the first elongated portion is different from the radius of curvature for the second elongated portion such that the elongated spinal prosthetic has a varying radius of curvature along its length.

13. The elongated spinal prosthetic of claim 12 wherein a thickness of the male connection mechanism is varied along its length.

14. The elongated spinal prosthetic of claim 13 wherein the thickness of the male connection mechanism is tapered along its length.

15. The elongated spinal prosthetic of claim 13 wherein the thickness of the male connection mechanism is stepped along its length.

16. The elongated spinal prosthetic of claim 12 wherein the radius of curvature for the first elongated portion is curved in a direction substantially opposite the radius of curvature for the second elongated portion when the first and second portions are connected.

17. The elongated spinal prosthetic of claim 12 further comprising a sleeve member positioned around the first and second elongated portions adjacent a junction between the first and second outer surfaces.

18. The elongated spinal prosthetic of claim 17 wherein the sleeve member comprises a clamp.

19. The elongated spinal prosthetic of claim 12 further comprising an end cap adapted to engage at least one end of at least one of the first and second elongated portions.

20. The elongated spinal prosthetic of claim 12 wherein the second elongated portion is molded over the first elongated portion.

21. The elongated spinal prosthetic of claim 12 wherein the first material is selected from the group of metals consisting of titanium alloys, cobalt-chromium alloys, nickel titanium alloys, and stainless steel alloys, and the second material is PEEK.

* * * * *